US006620110B2

(12) United States Patent
Schmid

(10) Patent No.: US 6,620,110 B2
(45) Date of Patent: Sep. 16, 2003

(54) HEARING AID IMPLANT MOUNTED IN THE EAR AND HEARING AID IMPLANT

(75) Inventor: Christoph Hans Schmid, Zollikon (CH)

(73) Assignee: Phonak AG, Stafa (CH)

(*) Notice: Subject to any disclaimer, the term of this patent is extended or adjusted under 35 U.S.C. 154(b) by 0 days.

(21) Appl. No.: 09/752,342

(22) Filed: Dec. 29, 2000

(65) Prior Publication Data

US 2002/0087094 A1 Jul. 4, 2002

(51) Int. Cl.$^{7}$ .................................................. A61B 5/00
(52) U.S. Cl. .......................... 600/559; 600/25; 381/328
(58) Field of Search ................................ 600/559, 136, 600/137, 25; 607/55, 56, 57; 381/312, 23.1, 324, 328

(56) References Cited

U.S. PATENT DOCUMENTS 3,882,285 A 5/1975 Nunley et al. ................ 600/25
4,729,366 A * 3/1988 Schaefer ...................... 600/25
5,338,287 A * 8/1994 Miller et al. .................. 600/25
5,460,593 A * 10/1995 Mersky et al. ................ 600/25
5,999,632 A * 12/1999 Leysieffer et al. .......... 381/328
6,077,215 A 6/2000 Leysieffer .................... 600/25
6,099,462 A * 8/2000 aWengen ..................... 600/25
6,137,889 A * 10/2000 Shennib et al. ............... 600/25
6,398,717 B1 * 6/2002 Leysieffer et al. ............ 600/25

FOREIGN PATENT DOCUMENTS

EP 0 936 840 A 8/1999

* cited by examiner

*Primary Examiner*—Willis R. Wolfe
(74) *Attorney, Agent, or Firm*—Pearne & Gordon LLP

(57) ABSTRACT

A hearing aid implant to be mounted in the ear includes a housing and an actuator mounted on the housing. The actuator is movable relative to the housing. An electromechanical drive transducer works between the housing and the actuator. The housing is attached to the outer ear part of the ear drum area and the actuator has an end facing away from the housing that works in the middle ear.

20 Claims, 6 Drawing Sheets

HEARING AID IMPLANT MOUNTED IN THE EAR AND HEARING AID IMPLANT

This invention concerns a hearing aid implant mounted in the ear according to the preamble to claim 1 and a hearing aid implant according to the one in claim 16.

If the organs in the ear that mechanically transmit vibrations are damaged and the transmission from the ear drum via hammer, anvil and stirrup no longer works on the oval window as it can in a person with normal hearing, the mechanical vibrations are purposely forced to work on one or more of the organs mentioned with the type of implants mentioned, corresponding to auditory signals received by a microphone arrangement in or outside the auditory canal. Even when there is inner ear damage, such implants are used: in that case, the mechanical vibrations on the oval window are amplified compared to normal hearing or altered in their frequency spectrum. This attempts to achieve the most optimal compensation for the inner ear damage. It is also conceivable for people basically even with normal hearing to wear an implant, especially when the application procedure is only minimal. Then audio signals from electric audio sources, like for example the Internet, MP3 players, CD players or conductive systems could be fed directly to the individual and finally to the implant as electrical signals. Also, predetermined desired hearing characteristics, like directional characteristics, can be made adjustable preferably on site with implants and microphones at the entrance to the ear, for both those with normal hearing and those with impaired hearing.

Thus, for example, it is known from U.S. Pat. No. 5,800,339 how to couple the type of implant mentioned to one of the organs mentioned in the middle ear. The implant consists of two masses that can move in relation to one another. The lighter of the two masses is connected to the organ, for example, one of the ossicles, while the second floats. The two masses are set in vibration electrically in relation to one another, corresponding to acoustic signals received. According to U.S. Pat. No. 5,558,618, it is known with an implant of the type mentioned above mounted in the ear how to mount a small permanent magnetic plate on one of the organs mentioned, especially on one of the ossicles, and to excite it mechanically without contact by a coil mounted directly in the ossicle area. One form of embodiment proposes building a microphone, a manually activated switching organ, batteries, amplifier and coil into a housing and putting it in the auditory canal in such a way that the coil is in turn adjacent to the area of a middle ear organ, especially like an ossicle, namely the hammer, to be set in vibration. This procedure requires the insertion of a relatively voluminous apparatus in the auditory canal, which is prepared accordingly and cleared up to the middle ear.

U.S. Pat. No. 5,906,635 also proposes providing a permanent magnetic disk on an ossicle and exciting vibrations via a coil mounted without contact in its direct area.

These implants that work on organs in the middle ear have the major disadvantage that they require extensive surgical procedures in the middle ear area itself and in the transitional area from the outer ear to the middle ear, i.e., in the stirrup area, to adapt the respective areas to the specifically selected implant techniques. Often a change from one implant technique to another is highly problematic, because outer and middle ear areas must be specifically adapted to the implant technique installed previously.

The problem of the invention is to propose a hearing aid implant of the type mentioned above mounted in the ear in which the application area, i.e., the outer and middle ear, is adapted only minimally invasively.

This is achieved on the above-mentioned type of hearing aid implant mounted in the ear by attaching the housing to the outer part of the ear in the stirrup area and having the end of the actuator facing away from the housing work in the middle ear.

This makes it possible to work from the outer ear area, through the stirrup area and finally into the middle ear with only a small passage to place housings with drive transducers in the outer ear area. The application procedure is normally done through the auditory canal. Because of the volume of the auditory canal and the simple surgical accessibility of the auditory canal wall area, this makes insertion of the housing with the drive transducer in it simple and minimally invasive. Also the actuator can be placed in the middle ear with only a minimal procedure, i.e., there are practically no implant-specific surgical adjustments to be made. This also makes it possible to change it or exchange it for another implant product.

In another preferred form of embodiment, the housing is mounted directly on the wall of the auditory canal or right next to it in the tissue of the wall of the auditory canal.

Although it is certainly possible to couple the end of the actuator mentioned anywhere in the middle ear anywhere effectively where mechanical vibrations ultimately affect the inner ear through the oval window, one preferred form of embodiment proposes anchoring the end of the actuator mentioned on one of the ossicles, either by a clip on the end of the actuator or by another known coupling technique that permits perfect transmission of vibrations to the respective ossicle.

In another preferred embodiment of the hearing aid implant mounted in the ear, the electromechanical drive transducer has an electrical input stage, which is attached to the housing. This has the advantage that electrical connecting lines from an acoustic-electrical transducer, which is not the subject of the invention, for example mounted outside the ear, are mechanically stationary. This bypasses the problem of stress changing these types of extremely thin electrical lines, and hence secondary acoustic interference signals caused by such mechanical vibrations as well.

Although in the following basically all known principles, if they are suitable by structural size, can be used as electromechanical drive transducers, like for example electrodynamic drive transducers, in the form of embodiment preferred today, the electromechanical drive transducer is designed as an electromagnetic or, if necessary, a piezoelectric drive transducer. These allow an extremely small structural design, which also allows it to be built like a little rod along an axis. This is an extremely good shape for insertion into the auditory canal wall or the tissue surrounding the auditory canal. Accordingly, the housing is preferably designed as a small tube and has an aperture on at least one of its front sides, from which the actuator goes out into the middle ear.

When the preferred electromechanical transducer is made as an electromagnetic drive transducer, preferably there is a coil arrangement stationary on the housing, and the actuator is mounted on a sliding bearing with a permanent magnetic part in the coil. Neodymium can be used, for example, as the permanent magnet material; this makes it possible to build extremely strong permanent magnets with low structural volume, for example Nd—Fe—B material.

In another preferred form of embodiment, the electrical input lines into the implant or its electromechanical drive transducer go along the auditory canal walls or into the tissue or bone bordering the auditory canal.

In another preferred form of embodiment of the implant in the invention, its actuator is spring-mounted in relation to the housing.

In another preferred embodiment, the housing, in its tube-shaped design mentioned with the actuator coming out of an aperture on the front, has a part tapering off in diameter toward the aperture mentioned. This makes it possible, in this tiny diameter part to move the actuator as far as possible mechanically toward its end mentioned, but still build this part, not needed for insertion of the electromechanical transducer, with minimal volume.

In another preferred embodiment, the housing is also designed to be tubular in shape, preferably as a rotational body, i.e., basically cylindrical, if necessary with steadily conically tapering parts.

It is also possible, in one preferred embodiment, to provide anchoring organs like ribs or nap on the housing to anchor it in the body tissue or bone material. No. 1 shows the length of the implant in the direction of transmission between the working end of the actuator, on one hand, and the end of the housing facing away from that end, so it preferably lies in the range of:

8 mm≦1≦30 mm, preferably in the range of 8 mm≦1≦15 mm, typically approximately 13 mm.

Preferably, the maximum diameter of the housing D is preferably chosen as follows:

2 mm≦D≦6 mm, preferably in the range of 2 mm≦D≦4 mm, typically approximately 3 mm.

The hearing aid implant in the invention in itself is characterized, to solve the above-mentioned problem, by the wording in claim 16, with preferred embodiments in claims 17 to 21.

The invention will now be explained using the figures.

Figure 1:
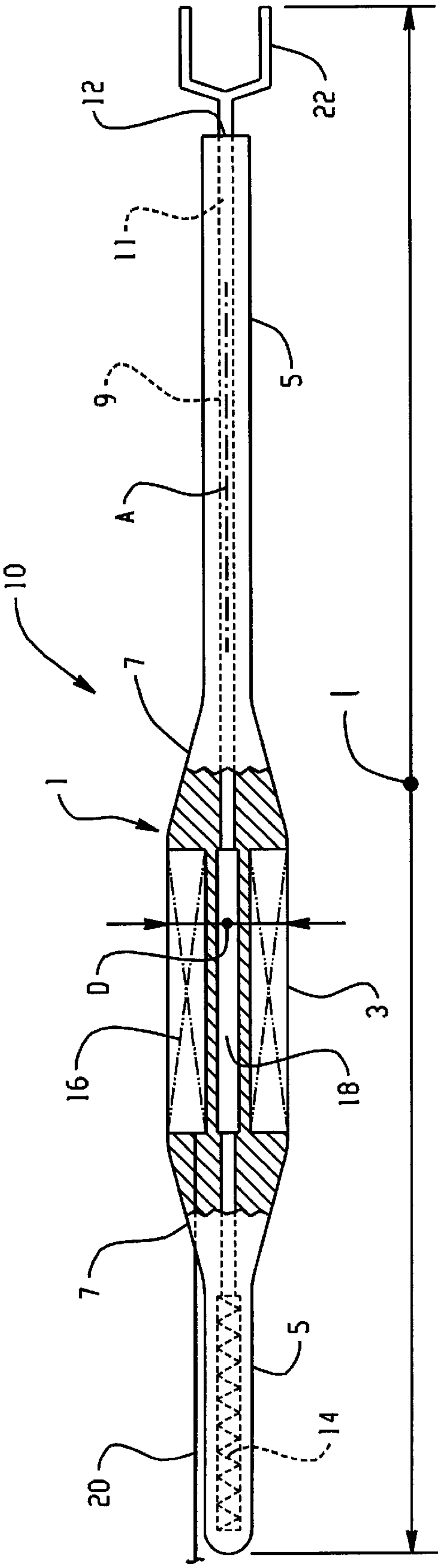
FIG. 1 shows the implant in the invention, partly sectioned and schematic, in a first preferred embodiment.
Figure 2:
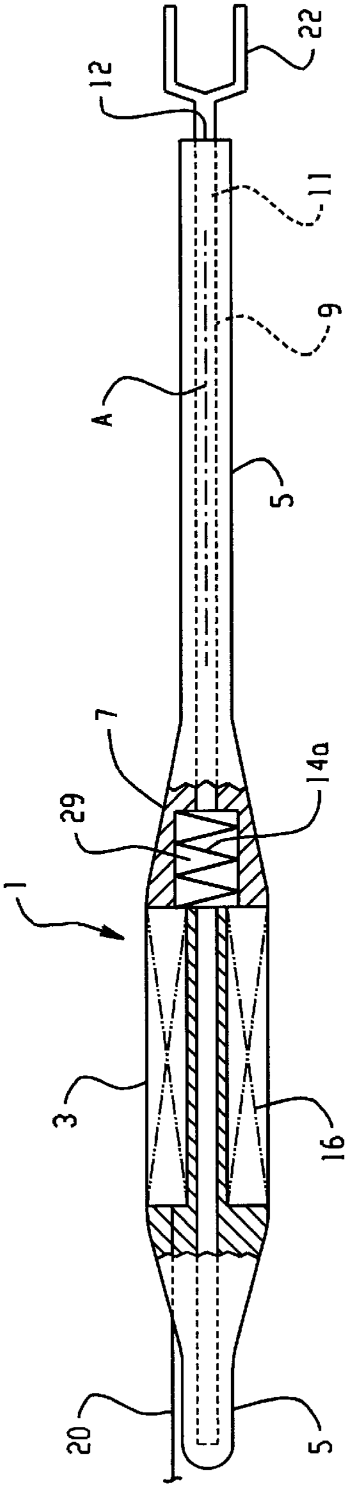
FIG. 2 shows another embodiment of the implant in the invention in a view similar to the one in FIG. 1.
Figure 3:
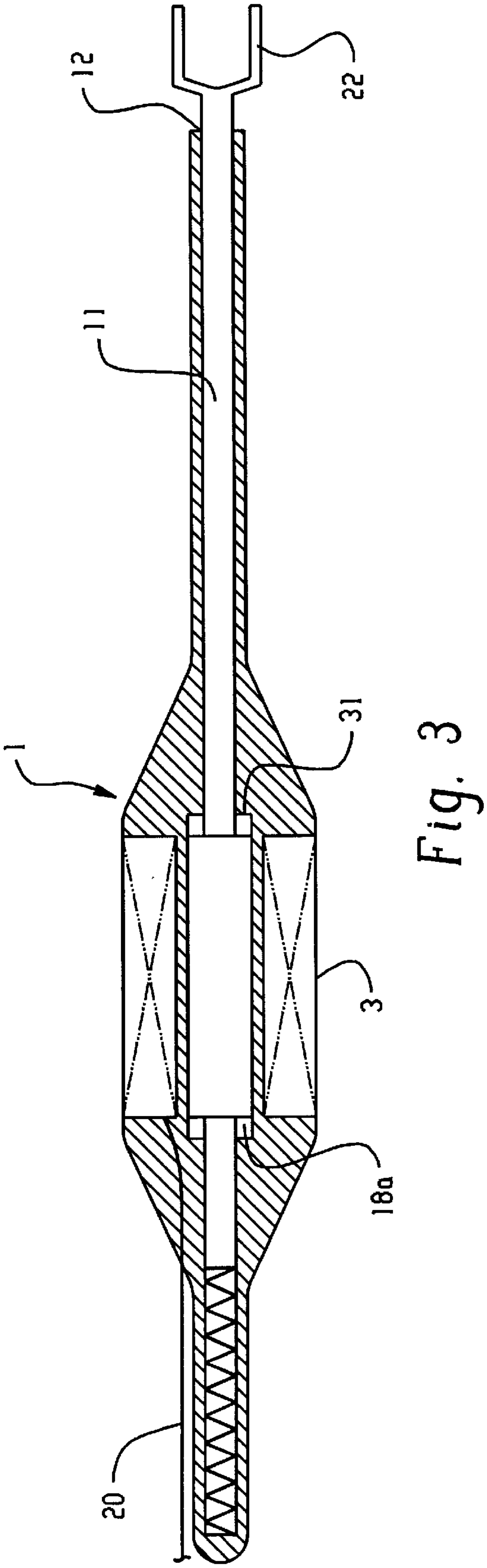
Figure 4:
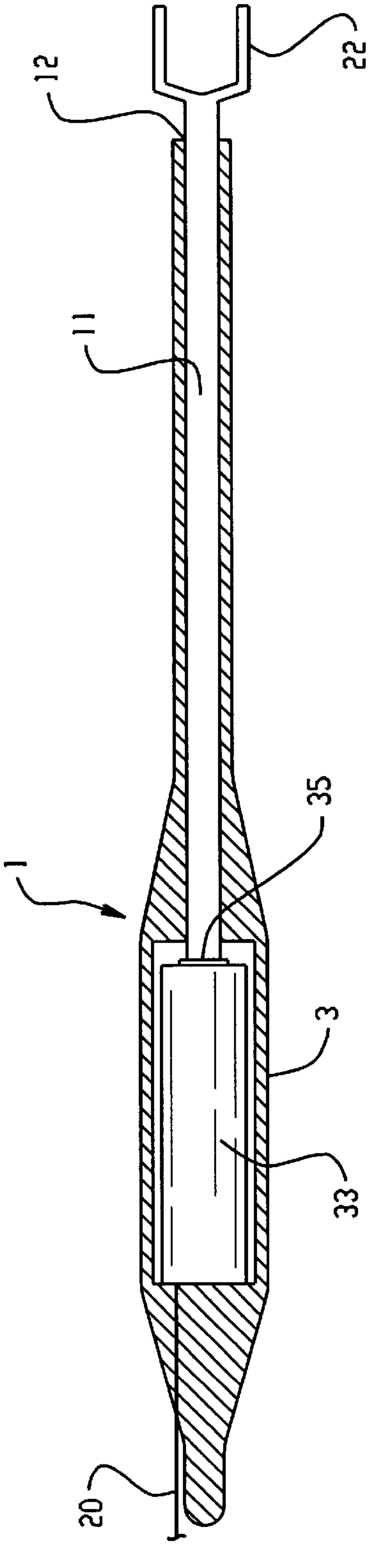
Figure 5:
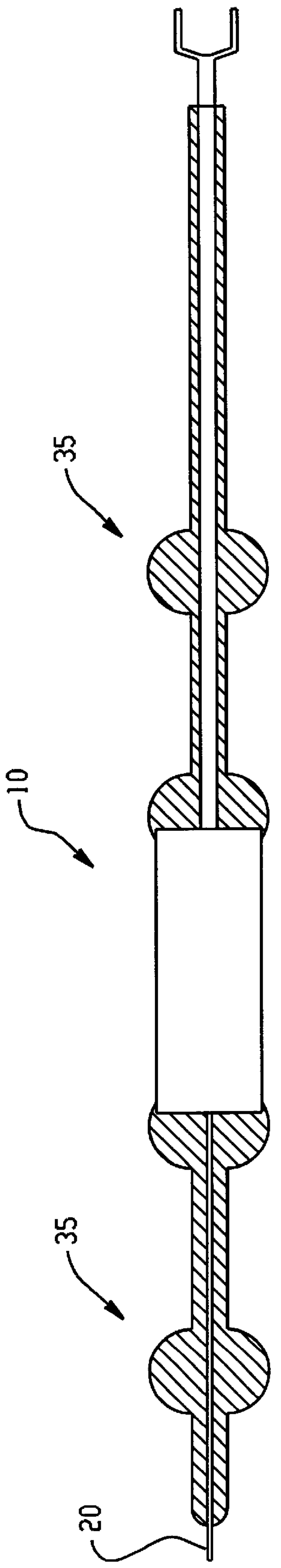
Figure 6:
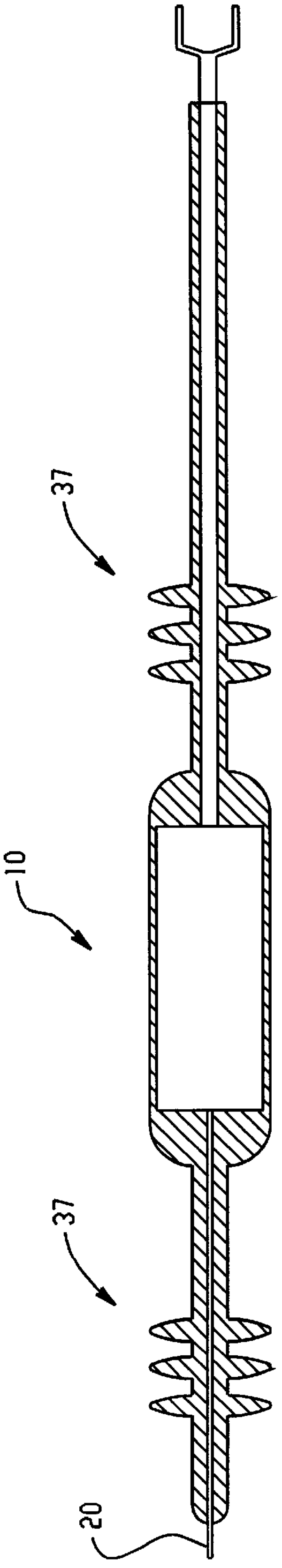
Figure 7:
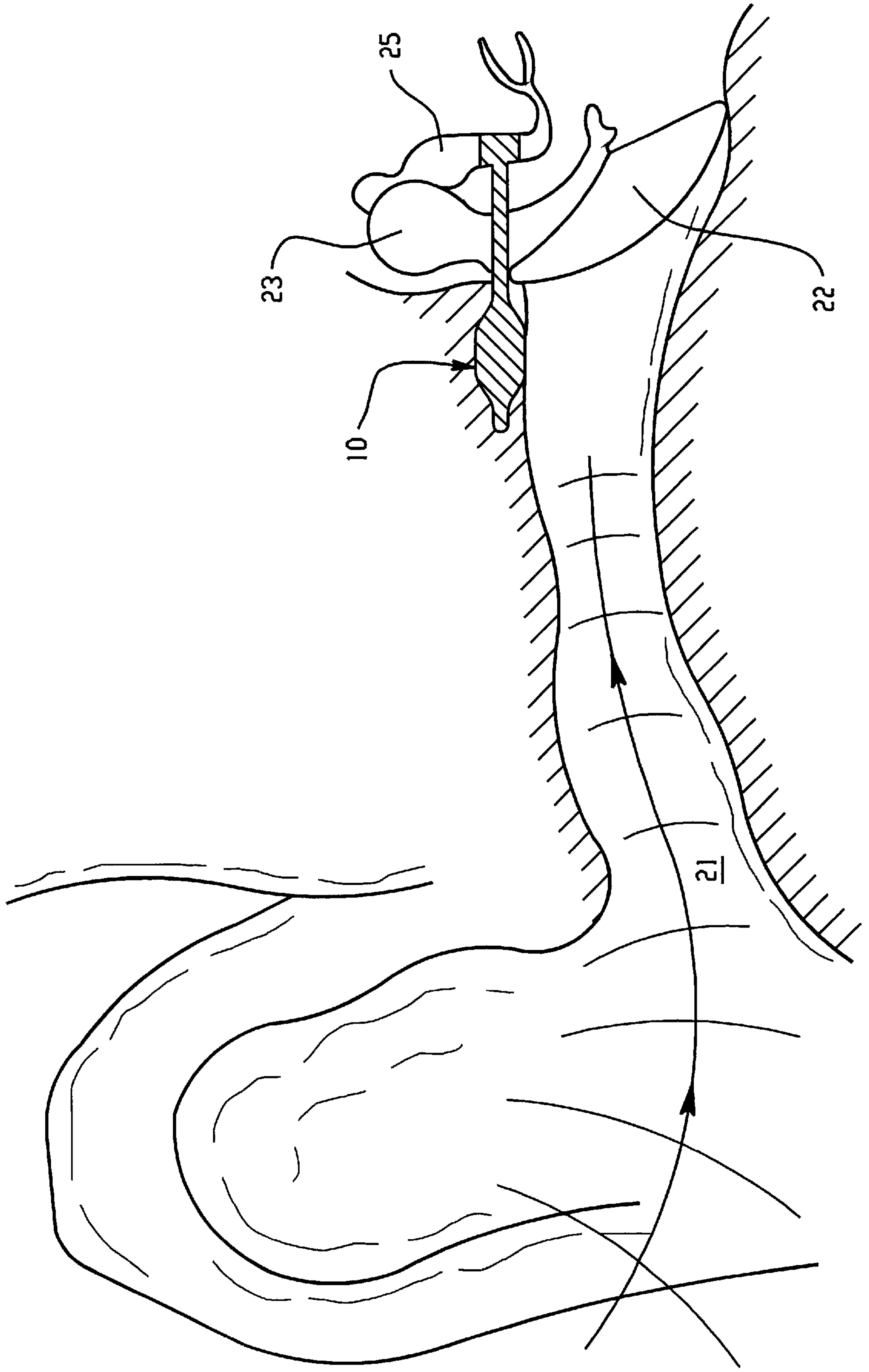
Figure 8A:
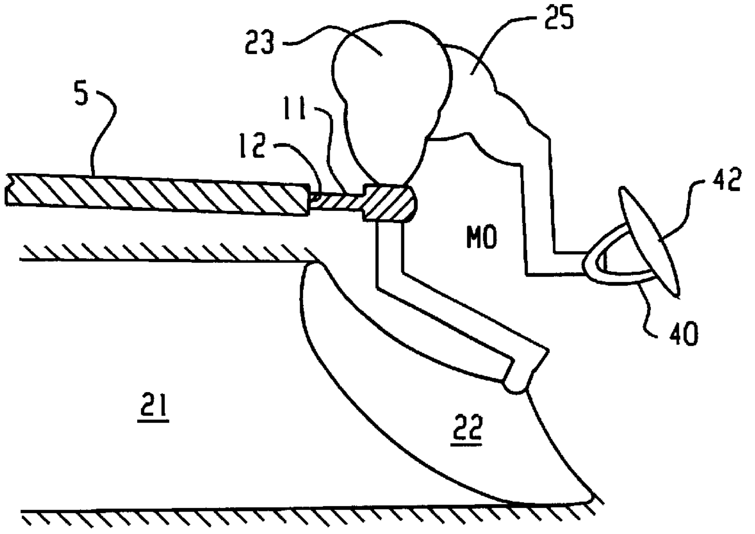
Figure 8B:
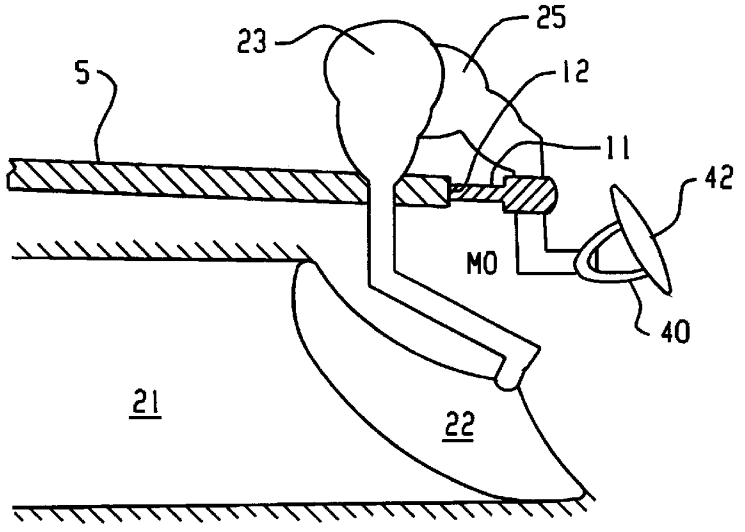
Figure 8C:
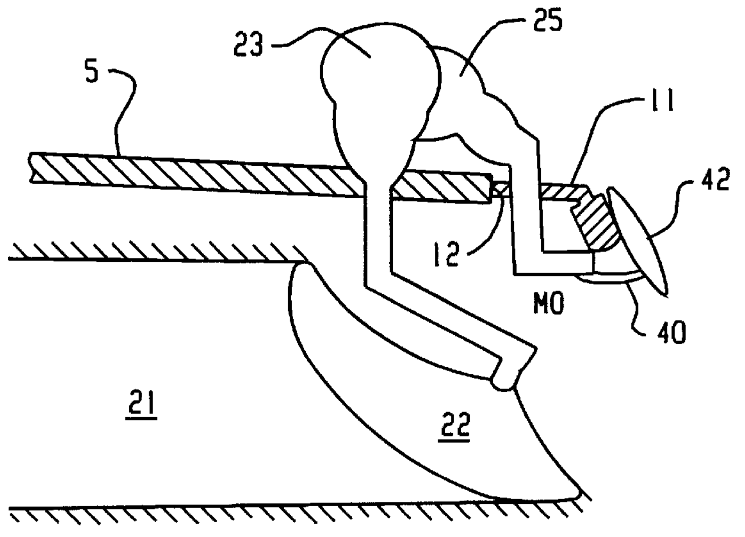
Figure 8D:
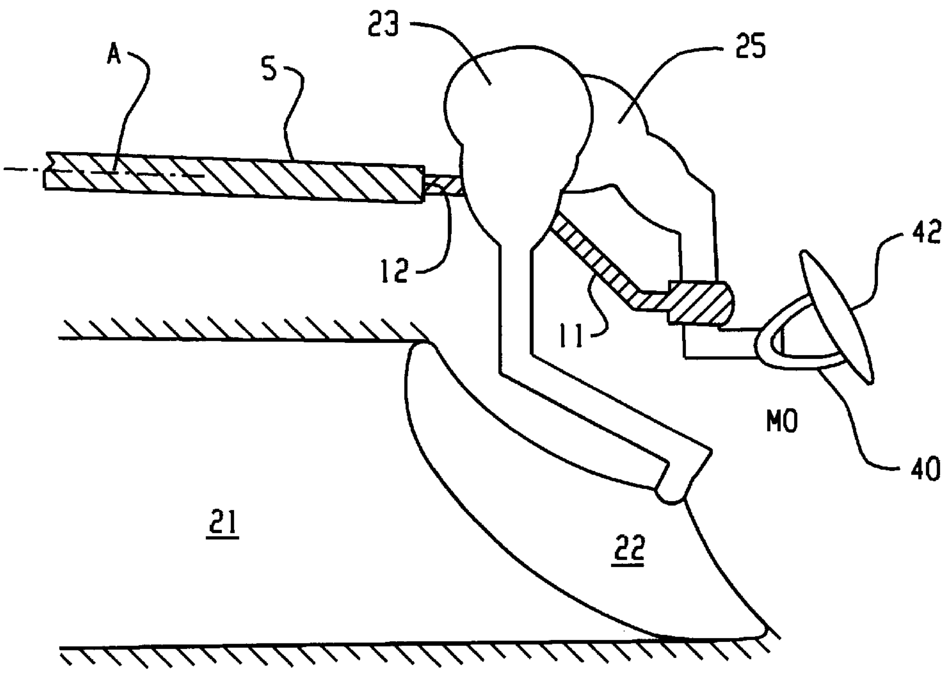
Figure 8E:
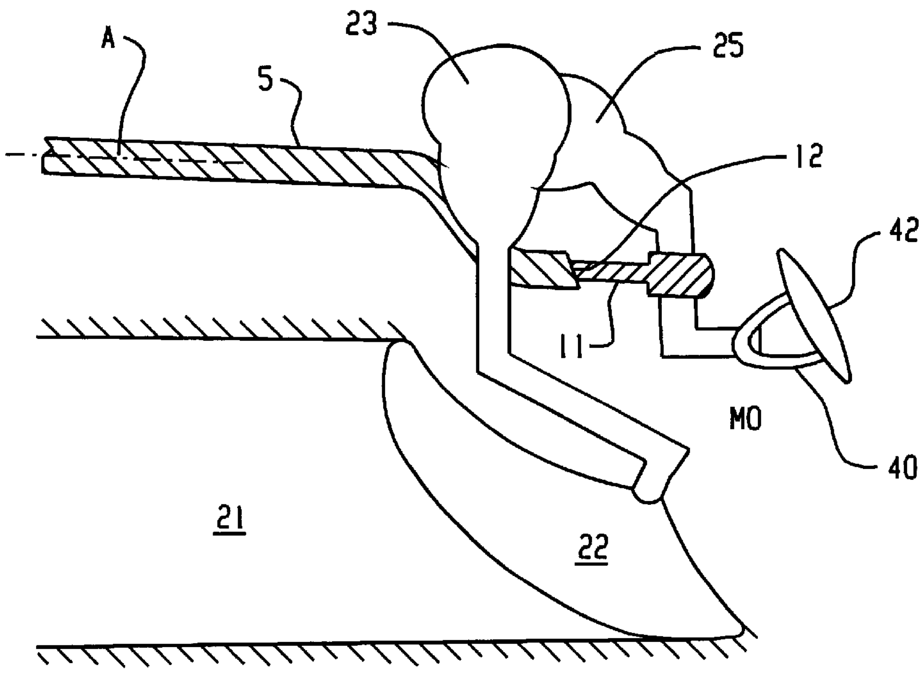

FIG. 3 in turn shows another embodiment of the implant in the invention in a view similar to the one in FIGS. 1 and 2;

FIG. 4 shows another embodiment of the implant in the invention with a piezoelectric drive transducer, also according to the view mentioned;

FIG. 5 shows the implant in the invention with anchoring organs for soft tissue;

FIG. 6 shows the implant in the invention with anchoring organs for bone tissue in a view similar to FIG. 5;

FIG. 7 shows the hearing aid implant in the invention built into the ear with an actuator coupling to the hammer on the end;

FIGS. 8*a* to 8*c* show schematically the coupling of the end of the actuator to the hammer, anvil or stirrup with a mechanically driven actuator;

FIG. 8*d* shows an alternate coupling possibility and geometric layout of the actuator on the anvil and FIG. 8*e* shows another actuator guide and hammer coupling.

The implant 10 has a basically cylindrical housing 1 with axis A. On a part 3, which has a relatively large diameter, sharply tapered actuator guide parts 5 are connected to transitional parts 7 that basically taper conically. The housing 1 is designed to be tubular in shape and has a coaxial guide bore hole 9 for an actuator 11. The bore hole extends from a housing aperture 12 on the front practically through the whole housing 1. The rod-shaped actuator 11 is mounted in this bore hole 9 with a slide bearing and is mounted on the end by means of a spring 14 in relation to the housing 1 and according to FIG. 1. A coil arrangement 16 is built into housing part 3, coaxial to axis A, and its magnetic field is connected to a permanent magnet area 18 on the actuator 11. Electrical connections 20 run to the outside toward the end of the housing 1 away from the aperture 12. The end of the actuator 11 projecting out of the aperture 12 has a coupling device, like a clip 22, as shown, if it needs to be coupled, for example to an ossicle in the middle ear.

A biocompatible material is used as the material, especially for the housing parts to be embedded on or in the body tissue, as will still be explained, such as for example titanium, platinum, tantalum, plastics like polyethylene, hydroxylapatite, ceramics or glass.

An attempt is made to minimize the field of scatter of the coil arrangement 16 in a way known, by embedding the coil arrangement in a covering (not shown) made of ferromagnetic material.

It should be taken into account that the acutator should transmit mechanical vibrations as distortion-free as possible in the longitudinal direction, so great stiffness is required in that direction. Perpendicular to the longitudinal direction, the actuator in operation can be exposed to shearing forces, so it should have a certain elasticity and a relatively high break strength in that direction. At least that part of the actuator which is exposed to body tissue should also be made of biocompatible material. Materials that can be considered for manufacturing the actuator or parts of it can therefore most easily be metals like titanium, tantalum, nitinol, etc.

By sending the output signal of an acoustic-electric transducer, which is placed for example outside the ear similar to an outside-the-ear hearing aid, through input lines 20, the coil arrangement 16 is excited, and the magnetic field concentrated in the area of axis A sets the actuator 11 in the corresponding vibrations via the permanent magnetic part 18. The vibrations are transmitted by the actuator 11 into the middle ear, for example, and in one preferred embodiment to one of the ossicles. Before other embodiments of the implant in the invention are presented, the implant mounted in the ear in the invention will be explained using FIG. 7. In FIG. 7,

21 shows the ear drum area of the auditory canal

22 shows the ear drum

23 shows the "hammer" ossicle

25 shows the "anvil" ossicle.

According to the invention, the implant 10 explained in one preferred embodiment using FIG. 1 is mounted with its housing 1, according to FIG. 1, in the auditory canal of the ear drum 22, i.e., on the outer ear, as shown, preferably embedded in the tissue surrounding the auditory canal. The actuator and, if necessary, the guide part 5, with a reduced diameter, which faces the aperture 12 in FIG. 1, goes through the ear drum area, so the end of the actuator 11 projects into the middle ear and there, as shown for example in FIG. 7, is connected to one of the ossicles, preferably the continuation of the anvil 25. The electrical input lines 20, not shown in FIG. 7, run outside along its wall to the outside or are embedded not very deep in the tissue surrounding the auditory canal. Because of the small aperture for the actuator 11 to go through in FIG. 1, from the outside into the middle ear and the coupling of the end of the actuator there, for example, to one of the ossicles, and the small-volume, longitudinally-extended shape of the implant housing with the drive, it is possible to insert the implant with only the least invasive procedures.

FIG. 2 shows another example of embodiment of the implant in the invention, which is different only in terms of the arrangement of the spring 14*a* described in FIG. 1. Instead of a spring 14, which works—according to FIG. 1—on one end of the actuator 11, in FIG. 2 a spring 14*a* is provided that works along the actuator between it and the housing 1, in a spring chamber 29 made for it in housing part 3.

FIG. 3 shows another embodiment of the implant in the invention. It differs from the one explained in FIG. 1 only by the fact that the permanent magnet part 18*a* of the actuator 11 has a larger diameter than the actuator part that comes out of the aperture 12 in the housing 1. The permanent magnet part 18*a* is in a transmission chamber 31 adjusted to its enlarged diameter in housing part 3. With it, it is possible, regardless of the geometric shape of the actuator 11 running to the outside into the middle ear, to dimension the permanent magnet part 18*a* so it corresponds to the desired magnetic transmission ratios.

In FIG. 4, a piezoelectric drive, not an electromagnetic drive, is built into the housing 1 of the implant in the invention. The housing of the implant is basically shaped the same as was already explained in FIGS. 1 to 3. The piezoelectric drive 33 is built into the drive part 3 of the housing 1 and—as shown in 35—coupled directly to the actuator 11.

In FIG. 5, on an implant 10 according to the invention, as was explained in FIGS. 1 to 4, there are anchoring forms 35 provided for soft tissue and in FIG. 6 anchoring forms 37 for bone tissue.

FIGS. 8*a* to 8*e* are the end sections of housing part 5 whose diameter is tapered, with the aperture 12, from which the respective actuator 11 projects into the middle ear. This schematic view also shows the auditory canal 21, the ear drum 22, the hammer 23, the anvil 25 and the stirrup 40 with the oval window 42. In FIG. 8*a,* the actuator which comes out of part 5 coaxially, for example motion-coupled with a clip or in another known way with the hammer 23, in FIG. 8*b* with the anvil 25, while the actuator 11 in FIG. 8*c* is kinked on the end and motion-coupled to the stirrup 40. As can be seen from FIGS. 8*d* and 8*e,* however, it is also possible to bend the area on the end of the tapered housing part 5 and/or the area on the end of the actuator 11 out of axis A in FIG. 1, with the kinked housing part 5, to make the corresponding area on the end of actuator 11 flexible for bending, for example as the end piece of a cable.

Looking back at FIG. 1, the implant in the invention in one preferred embodiment is dimensioned as follows: The length 1 between the coupling end 22 of the actuator 11 and the end of the housing 1 facing away is chosen in the following range:

8 mm≦1≦30 mm, preferably in the range of 8 mm≦1≦15 mm, typically approximately 13 mm.

the maximum diameter D of the housing 1 is in the following range:

2 mm≦D≦5 mm, preferably 2 mm≦D≦4 mm, typically approximately 3 mm.

It should be emphasized that the vibration stroke made in practice by the actuator 11 is so small that it is negligible in relation to the length 1 mentioned.

With the implant proposed by the invention by itself or inserted in the ear, only minor surgical procedures need to be undertaken on the ear, basically on the outer ear only to anchor the implant housing and in the middle ear to anchor the actuator at the place provided. To transmit movement from the outer ear of the housing to the middle ear of the actuator end requires only a small opening through the ear drum area.

What is claimed is:

1. A hearing aid implant comprising:

a housing;

an actuator having an end, wherein the actuator is mounted in the housing so that the actuator can move in relation to the housing; and an electromechanical drive transducer working between the housing and the actuator, wherein the housing is attached on or in the wall of an auditory canal and a movement of the actuator within the housing is transmitted by the actuator to the end, and further wherein the motion of the transducer is on or about the same axis as the motion of the end.

2. A hearing aid implant for mounting in an ear, the implant comprising a housing (1), an actuator (11) mounted in the housing so that the actuator so that the actuator can move in relation to the housing and an electromechanical drive transducer (16, 33) working between the housing (1) and the actuator (11), wherein the housing (1) is attached on or in the wall of an auditory canal and a movement of the actuator within the housing is transmitted by the actuator to a substantially equal movement of an end of the actuator.

3. The hearing aid implant in claim 1 wherein the end of the actuator is anchored to one of the ossicles.

4. The hearing aid implant in one of claim 1, wherein the electromechanical drive transducer has an electrical input stage (16) that is attached to the housing.

5. The hearing aid implant in one of claim 1, wherein the electromechanical drive transducer is an electromagnetic drive transducer.

6. The hearing aid implant in claim 1, wherein the housing is designed to be tubular in shape and has an aperture (12) on at least one of its front sides.

7. The hearing aid implant in claim 6, wherein a coil arrangement (16) is provided on the housing (1), and the actuator (11) is mounted with a slide bearing in the coil with a permanent magnet part (18).

8. The hearing aid implant in one of claim 7, wherein electrical input lines (20) to the electromechanical drive transducer run along the wall of the auditory canal or in the adjacent tissue or bone.

9. The hearing aid implant in one of claim 7, wherein the electromechanical drive transducer is a piezoelectric drive transducer.

10. The hearing aid implant in one of claim 7, wherein the actuator is spring-mounted (14, 14*a*) so it can move in relation to the housing.

11. The hearing aid implant in one of claim 7, wherein the housing has a part (5) whose diameter is tapered toward the aperture (12).

12. The hearing aid implant in one of claim 7, wherein the housing has the shape of a rotating body and is preferably basically cylindrical.

13. The hearing aid implant in one of claim 7, wherein anchoring organs (35, 37) on the housing are provided to anchor it in the body tissue and/or bone.

14. The hearing aid implant in one of claim 7, wherein the length (1) between the effective end of the actuator and the end of the housing facing away from it lies in the following range:

8 mm<1<30 mm, preferably in the range 8 mm<1<15 mm, typically approximately 13 mm.

15. The hearing aid implant in one of claim 7, wherein the maximum diameter of the housing (d) lies in the following range:

2 mm<D<5 .mm, preferably 2 mm<D<4 mm, typically approximately 3 mm.

16. A hearing aid implant comprising a housing (1), an actuator mounted on it so it can move in relation to the housing (1), and an electromechanical drive transducer working between the housing (1) and the actuator (11), characterized by the fact that the housing is designed to be tubular in shape and has an aperture (12) on at least one of its front sides, and the actuator (11) is mounted so it can move in the housing and projects through the aperture (12), and wherein the actuator (11) has a coupling arrangement (22) for one of the ossicles on its end facing away from the housing (1).

17. The implant in claim 16, wherein the electromechanical drive transducer is an electromagnetic drive transducer.

18. The implant in claim 16, wherein the electromechanical drive transducer is a piez6 drive transducer.

19. The implant in claim 16, wherein a coil arrangement (16) coaxial to the axis of the housing is provided on the housing (1) with electrical connections (20) that run to the outside and by the fact that the actuator (11) has a permanent magnet part (18) that is slide-mounted in the housing (1), preferably spring mounted (14, 14*a*).

20. The implant in claim 16, wherein anchoring organs (35, 37) like ribs are provided on the outside of the housing (1) to anchor the implant in the wall tissue or bone of the auditory canal.

* * * * *